United States Patent [19]

Sugawara et al.

[11] Patent Number: 5,768,465

[45] Date of Patent: Jun. 16, 1998

[54] ALTERNATIVE DISPLAY STATE MEDICAL PHOTOGRAPHIC INSTRUMENT

[75] Inventors: Takao Sugawara; Hiroaki Okada; Yutaka Yoneda, all of Tokyo, Japan

[73] Assignee: Kabushiki Kaisha Topcon, Tokyo, Japan

[21] Appl. No.: 365,358

[22] Filed: Dec. 28, 1994

[30] Foreign Application Priority Data

Dec. 28, 1993 [JP] Japan .................... 5-334720

[51] Int. Cl.⁶ .................... H04N 5/76; H04N 7/18
[52] U.S. Cl. .................... 386/46; 348/78; 348/371
[58] Field of Search .................... 348/78, 371; 358/335, 358/342; 360/33.1; 351/200, 221; 386/1, 45–46, 125–126; H04N 7/18, 9/47, 5/222, 5/76

[56] References Cited

U.S. PATENT DOCUMENTS

| | | | |
|---|---|---|---|
| 3,915,564 | 10/1975 | Urban | 351/206 |
| 4,018,514 | 4/1977 | Plummer | 351/206 |
| 4,208,107 | 6/1980 | Oharek | 351/206 |
| 4,877,322 | 10/1989 | Hill | 351/221 |
| 5,347,331 | 9/1994 | Isogai et al. | 351/221 |
| 5,530,493 | 6/1996 | Suzuki | 351/206 |

Primary Examiner—Thai Tran
Attorney, Agent, or Firm—Finnegan, Henderson, Farabow, Garrett & Dunner, L.L.P.

[57] ABSTRACT

A medical photographic instrument includes a medical photographic portion and an electronic image recording portion. The medical photographic portion includes a monitor for displaying an observation image for alignment and a record image recorded in the electronic image recording portion and a display selecting circuit for making an alternate change between the observation image and the record image displayed on the monitor. The electronic image recording portion includes an operation changing circuit for making an alternate change between a recordable state and an image recording state according to a signal output by the medical photographic portion and a strobe synchronous circuit for outputting a strobe synchronizing signal according to which a strobe emits a flash of light when the recordable state is changed to the image recording state. The display selecting circuit makes an alternate change between the state in which the observation image is displayed and the state in which the record image is displayed in accordance with the signal output by the medical photographic portion.

1 Claim, 8 Drawing Sheets

ALTERNATIVE DISPLAY STATE MEDICAL PHOTOGRAPHIC INSTRUMENT

BACKGROUND OF THE INVENTION

1. Field of the Invention

This invention relates to a medical photographic instrument, such as a fundus camera, for use in ophthalmological or medical examination and treatment.

2. Description of the Prior Art

Heretofore, a medical image photographic instrument is known which includes a medical photographic portion, such as a fundus camera, and an electronic image recording portion, such as a still video recorder or a video printer. In the medical image photographic instrument, the medical photographic portion is provided with a TV camera and display means. The display means serves to display an image (called an observation image) for alignment which is observed in accordance with a photographic image signal outputted from the TV camera and serves to display an image (called a record image) which is recorded in the electronic image recording portion in accordance with the photographic image signal. The medical photographic portion is further provided with a photography switch and a selection switch for changing an image displayed on the display means from an image for recording to an image for observation.

In the conventional medical image photographic instrument, a strobe emits a flash of light when operating the photography switch, and thereby a photographic image signal is outputted to the electronic image recording portion. When the electronic image recording portion is in a recordable state in which the electronic image recording portion can receive a signal, a photographic image is recorded as a recorded image in the electronic image recording portion, in accordance with the photographic image signal, and the electronic image recording portion is brought to an image recording state in which the record image is outputted to the display means. Thereby, an image on the display means is changed from the observation image to the record image. When the record-to-observation changing switch is operated, the image on the display means is changed again from the record image to the observation image.

However, since the photography switch and the display selection switch are individually mounted in the conventional instrument, there are frequent occasions when an operator hesitates about which switch should be operated in photography.

For this reason, studies have been made of a medical image photographic instrument in which the display selection can be carried out by operating a single photography switch. In this medical image photographic instrument, the electronic image recording portion includes a strobe synchronous circuit. The medical image photographic instrument is constructed to actuate the strobe synchronous circuit by operating the photography switch when the electronic image recording portion is in a recordable state in which the electronic image recording portion can receive a signal from the medical photographic portion and output a strobe synchronizing signal to the medical photographic portion so that the strobe of the medical photographic portion emits a flash of light.

However, there are cases in which this electronic image recording portion reaches an unrecordable condition for the following reasons, for example:

(1) the power supply of the recording portion is shut off when the observation image is displayed on the screen, (2) the recording portion is in an initial condition immediately after the electric power is supplied, or (3) a floppy disk is not inserted in, for example, a still video recorder which makes up the recording portion.

If the photography switch is operated by mistake in these cases, a strobe synchronizing signal is not generated and accordingly the strobe does not emit a flash of light because the strobe synchronous circuit of the electronic image recording portion is not actuated. On the other hand, the medical photographic portion is actuated by operating the photography switch, and the display means changes the image displayed thereon from the observation image to the record image.

Let it be supposed that the operator notices this trouble and brings the displayed image into a recordable state by, for example, supplying the electric power to the electronic image recording portion. After that, the operator again operates the photography switch so that the display means can change the displayed image from the record image displaying state to the observation image displaying state. Just at that time, a strobe synchronizing signal is output from the electronic image recording portion regardless of the change from the record image displaying state to the observation image displaying state. Accordingly, although the operator has no intention of photographing, the strobe emits a flash of light.

SUMMARY OF THE INVENTION

It is therefore an object of the present invention to provide a medical photographic instrument which is convenient to change a display means from an observation image displaying state to a record image displaying state by operating a sole photography switch and has a practical advantage that an alternate change can be made between the observation image and the record image displayed on the display means without destroying the timing of light emission of a strobe.

It is a second object of the present invention to provide a medical photographic instrument capable of preventing the display means from changing a displaying state when an electronic image recording portion is out of a recordable condition by reason of, for example, its initial condition.

It is a third object of the present invention to provide a medical photographic instrument capable of advantageously emitting flashes of light from a strobe without mistaking the timing of its emission when an alternate change is carried out between the observation image and the record image displayed on the display means.

To achieve the objects, the medical photographic instrument according to an aspect or the present invention includes a medical photographic portion and an electronic image recording portion. The medical photographic portion includes a display means for displaying an observation image for alignment and a record image recorded in the electronic image recording portion and a display selecting means for making an alternate change between the observation image and the record image displayed on the display means. The electronic image recording portion includes an operation changing means for making an alternate change between a recordable state and an image recording state according to a signal output by the medical photographic portion and a strobe synchronous means for outputting a strobe synchronizing signal for emitting a flash of light from a strobe when the recordable state is changed to the image recording state. The display selecting means makes an alternate change between the state in which the observation image is displayed and the state in which the record image is displayed according to the signal output by the medical photographic portion.

According to the medical photographic instrument, when an observation image is displayed on the display means and the electronic image recording portion is in a recordable state, the electronic image recording portion outputs a strobe synchronizing signal by operating the photography switch. Thereby, the strobe emits a flash of light, and then a photographic image is recorded In the electronic image recording portion. At the same time, in the recording portion, the recordable state is changed to the image recording state.

Further, in the display means, the state in which an observation image is displayed is changed to the state in which a record image is displayed according to a signal generated by the operation of the photography switch. When the photography switch is further operated, the image recording state of the electronic image recording portion is changed to the recordable state. At the same time, the record image displaying state of the display means is changed to the observation image displaying state.

To achieve the objects, the medical photographic instrument according to another aspect of the present invention includes a medical photographic portion and an electronic image recording portion. The medical photographic portion includes a display means for displaying an observation image for alignment and a record image recorded in the electronic image recording portion and a display selecting means for making an alternate change between the observation image and the record image displayed on the display means. The electronic image recording portion includes an operation changing means for making an alternate change between a recordable state and an image recording state according to a signal output by the medical photographic portion and a strobe synchronous means for outputting a strobe synchronizing signal according to which a strobe emits a flash of light when the recordable state is changed to the image recording state. The display selecting means receives a record-to-observation changing signal according to a signal output by the medical photographic portion and receives an observation-to-record changing signal according to the strobe synchronizing signal. The display means is brought to the observation image displaying state when the display selecting means receives the record-to-observation changing signal only, whereas the display means is brought to the record image displaying state when the display selecting means receives both of the record-to-observation changing signal and the observation-to-record changing signal.

According to the medical photographic instrument, by operating the photography switch when an observation image is displayed on the display means and the electronic image recording portion is out of a recordable state by reason of, for example, no power supply, the first control circuit outputs an operation changing signal to the electronic image recording portion and, at the same time, outputs a record-to-observation changing signal to the display selecting means. However, a strobe synchronizing signal is not outputted since the electronic image recording portion is out of a recordable state. The observation image remains displayed since the observation image has been already displayed on the display means.

After that, the electronic image recording portion is brought to the recordable state by, for example, turning on the electric power. When the photography switch is operated, the electronic image recording portion is changed from the recordable state to the image recording state in accordance with the operation changing signal generated by the first control circuit. Thereby, a strobe synchronizing signal is outputted from the strobe synchronous circuit to the second control circuit. In accordance with this strobe synchronizing signal, the second control circuit outputs a strobe flashing signal to the medical photographic portion, and thereby the strobe emits a flash of light. Thus, photography is carried out and a photographic image is then recorded as a record image in the electronic image recording portion. Additionally, in accordance with the strobe synchronizing signal, the second control circuit outputs an observation-to-record changing signal to the display selecting means. Thereby, the display on the display means is changed from the observation image to the record image.

When the photography switch is operated again, the first control circuit outputs an operation changing signal to the electronic image recording portion and, at the same time, outputs a record-to-observation changing signal to the display selecting means. In accordance with the operation changing signal, the electronic image recording portion is changed from the electronic image recording state to the recordable state, but a strobe synchronizing signal is not outputted. The display on the display means is changed from the record image to the observation image.

Further, according to the medical photographic instrument, the displaying state of the display means is changed according to information about observation and record which is output by the electronic image recording portion.

To achieve the objects, the medical photographic instrument according to still another aspect of the present invention includes a medical photographic portion, an electronic image recording portion, and a display selecting means. The medical photographic portion includes a display means for displaying an observation image for alignment and a record image recorded in the electronic image recording portion. The electronic image recording portion includes an operation changing means for making an alternate change between a recordable state and an image recording state according to a signal output by the medical photographic portion and a strobe synchronous means for outputting a strobe synchronizing signal for emitting a flash of light from a strobe when the recordable state is changed to the image recording state. According to the signal generated when the medical photographic means performs photography, the display selecting means makes an alternate change between the observation image and the record image each displayed on the display means.

DETAILED DESCRIPTION OF THE PREFERRED EMBODIMENTS

First Embodiment

Figure 1:
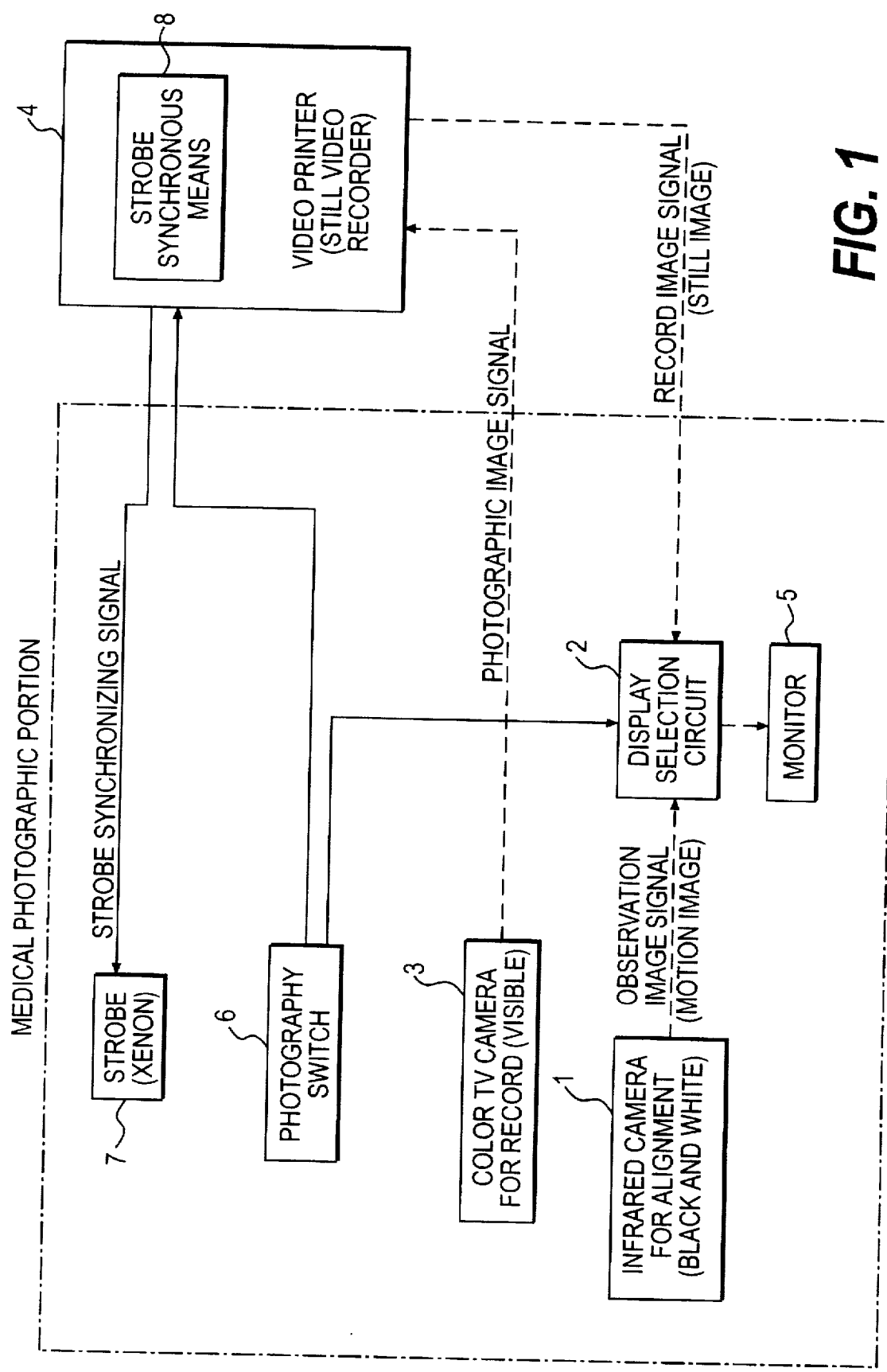
FIG. 1 is a block diagram schematically showing the construction of a medical photographic instrument according to a first embodiment of the present invention.

In a fundus camera of the present invention seen in FIG. 1, as shown in FIG. 1 an observation image is photographed with the infrared camera 1 so as not to constrict the pupil of the eye. An operator looks at the observation image, while carrying out alignment for focusing. The fundus camera is connected to a monitor 5 as a display portion through a display selection circuit 2 shown in FIG. 1. An observation image sent from the infrared camera 1 and a record image sent from a video printer 4 are alternately displayed on the monitor 5 by means of the display selection circuit 2 whenever the photography switch 6 is pushed. The regenerated record image in used to ascertain a photographic condition.

The still video recorder 4 includes an operation selecting means for making an alternate change between a recordable state and image recording state in accordance with a selecting signal output whenever the photography switch is pushed. The strobe or xenon lamp 7 emits a flash of light by means of a strobe synchronous circuit 8 when recorded or photographed. The strobe synchronous circuit 8 is beforehand built in the still video recorder 4. When the photography switch 6 is pushed, the strobe synchronous circuit 8 outputs an emission signal according to which the strobe 7 emits a flash of light every other tine synchronously with the display selection circuit 2 and the operation selecting means. When photography is carried out with the flash of light, a record image recorded in the still video recorder 4 is displayed on the monitor 5.

The action of the first embodiment will now be described.

Let it be supposed that an observation image is displayed on the monitor 5 and the still video recorder 4 is in a recordable condition. If the photography switch 6 is operated at this time, the still video recorder 4 outputs a strobe synchronizing signal recording to a signal generated by the operation of the photography switch 6. Thereby, the strobe 7 emits a flash of light. After that, a photographic image signal is output by the color TV camera 3, and then the photographic image is recorded in the still video recorder 4 and, at the same time, the still video recorder 4 is brought into the image recording condition from the recordable condition.

Since the display selection circuit 2 is switched according to the signal generated by the operation of the photography switch 6, the photographic image is displayed on the monitor 5. Next, the still video recorder 4 is brought into the recordable condition from the image recording condition in accordance with a signal generated by further operating the photography switch 6. Since the observation image instead of the photographic image is electrically connected to the monitor 5, the observation image is again displayed on the monitor 5. As mentioned above, both of the photography and the display change of the images displayed on the monitor 5 can be carried out by operating the sole photography switch 6.

Second Embodiment

Figure 2:
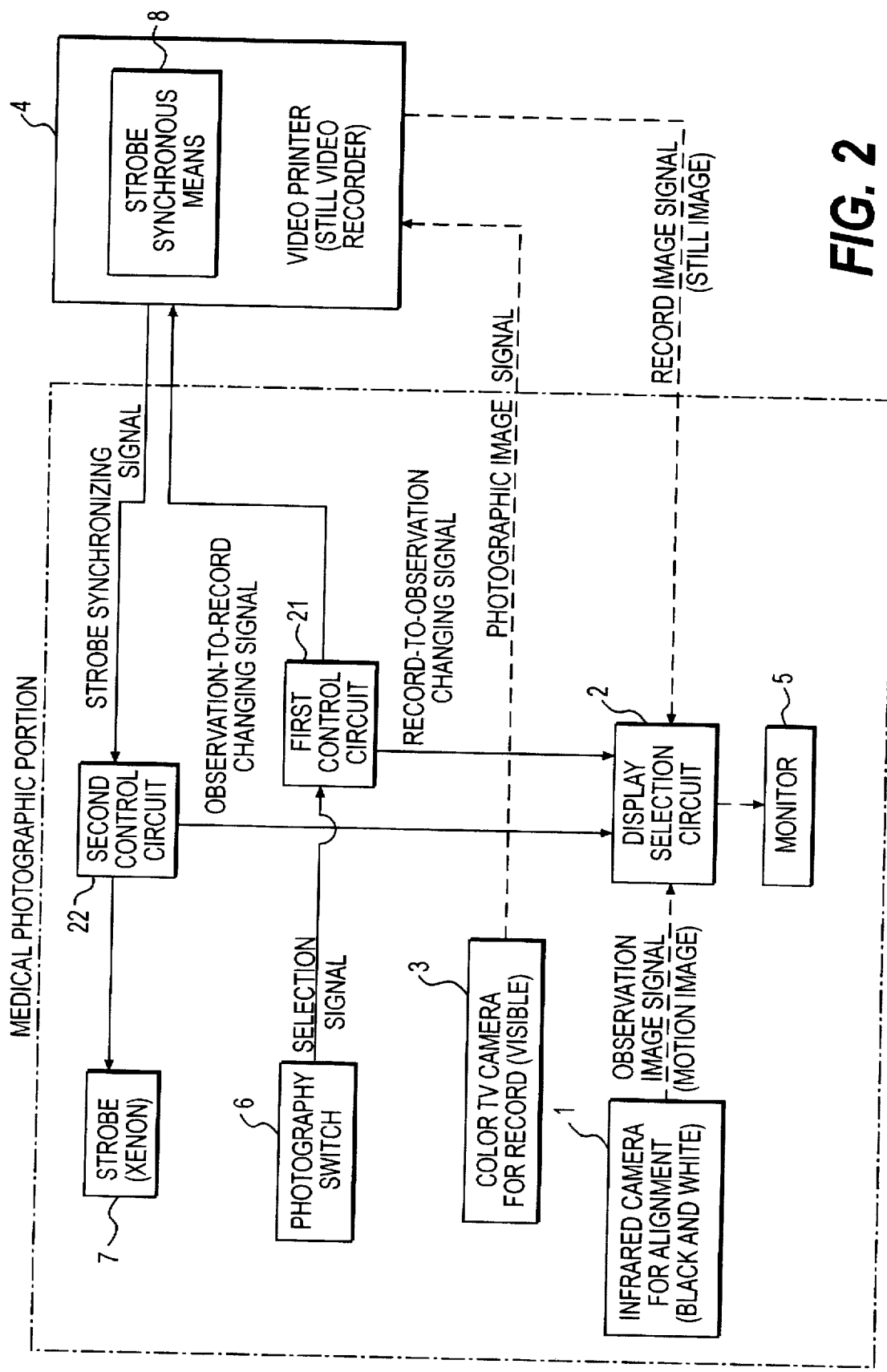
FIG. 2 is a block diagram schematically showing the construction of a medical photographic instrument according to a second embodiment of the present invention.
Figure 3:
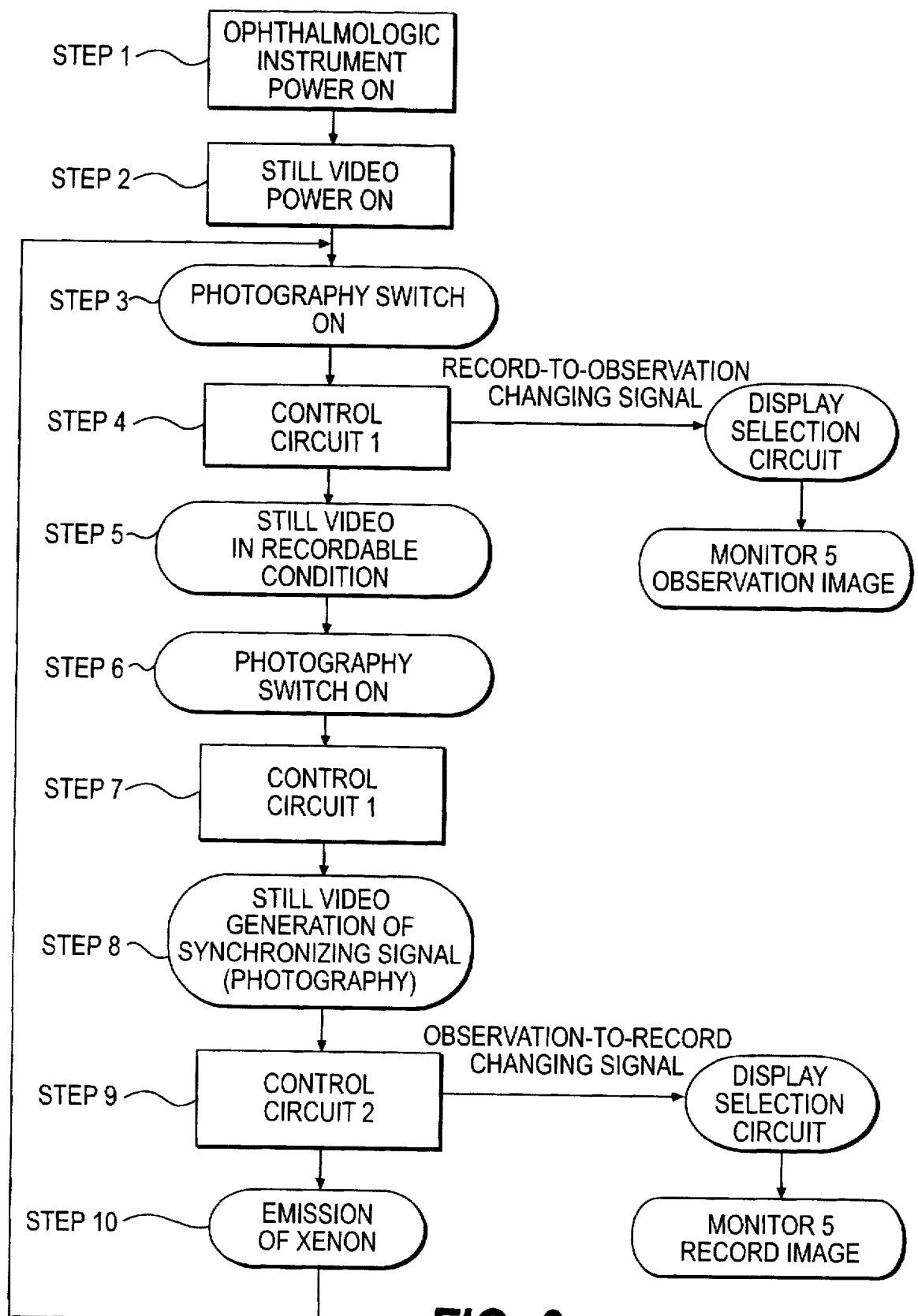
FIG. 3 is a flow chart of the action of the medical photographic instrument according to the second embodiment, showing a case in which a still video recorder as an electronic image recording portion is connected to the instrument.
Figure 4:
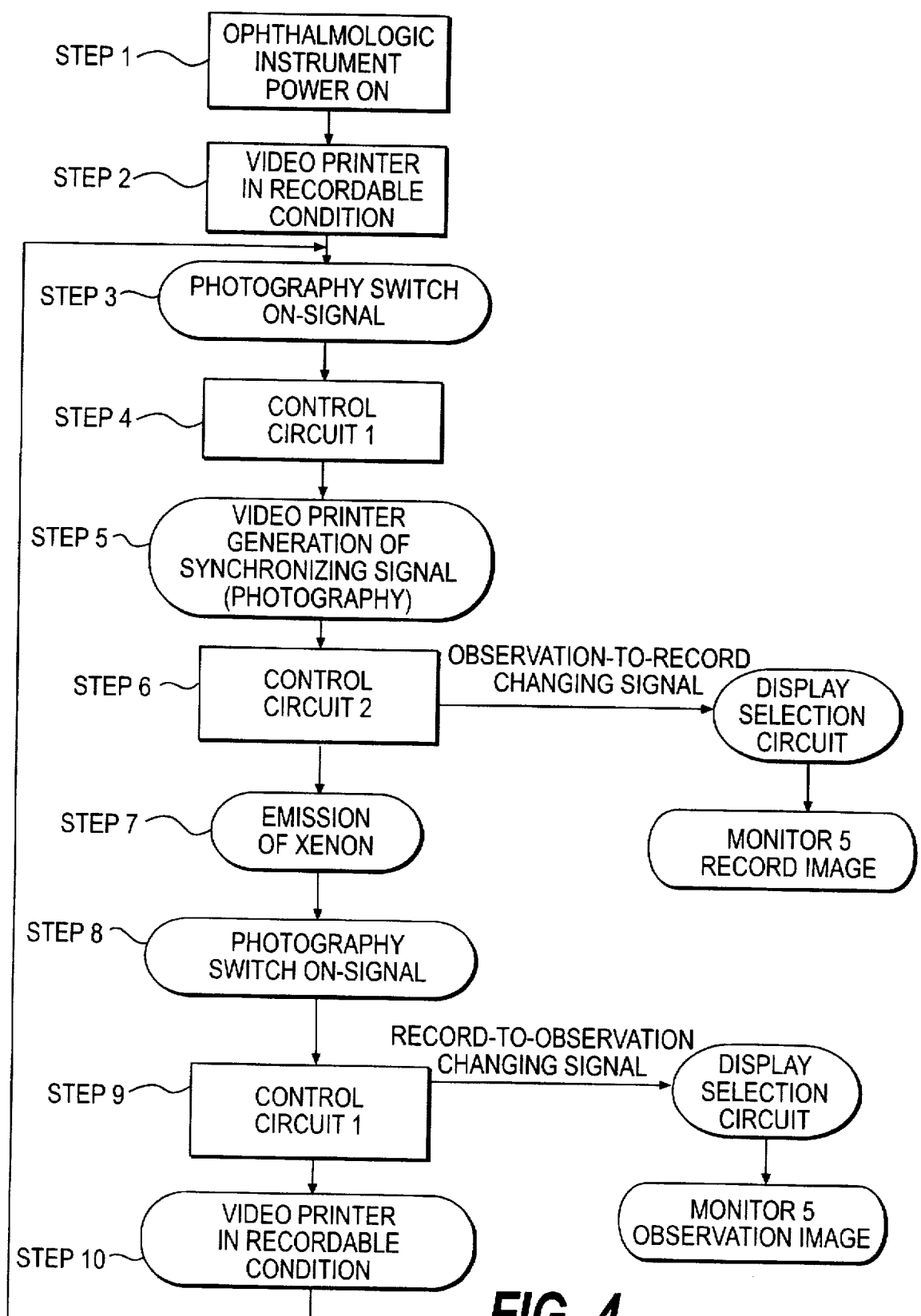
FIG. 4 is a flow chart of the action of the medical photographic instrument according to the second embodiment, showing a case in which a video printer as the electronic image recording portion is connected to the instrument.

FIGS. 2 to 4 show a second embodiment of the present invention

The arrangement of optical members of a medical photographic instrument in this embodiment is almost the same as in the first embodiment. Therefore, a detailed description of them is omitted, and the difference between the first and second embodiments will be hereinafter described.

In the second embodiment, as shown in FIG. 2, the photography switch 6 is connected to the still video recorder 4 through a first control circuit 21. The first control circuit 21 receives a signal generated by operating the photography switch 6, and then outputs a record-to-observation changing signal, according to which a displayed image is changed from a record image to an observation image, to the display selection circuit 2.

The still video recorder 4 is further provided with an operation changing means for making an alternate change between a recordable condition (REC standby) and an image recording condition in accordance with a signal generated by operating the photography switch 6. The still video recorder 4 is constructed to record the record image under the image recording condition and then output a record image signal to the display selection circuit 2. Further, the still video recorder 4 selects a recordable condition when the recorder 4 is in an initial conditions. When the photography switch 6 is pushed, the strobe synchronous circuit 8 outputs a strobe synchronizing signal for the light emission of the strobe 7 to a second control circuit 22 under the recordable condition. Under the image recording condition, the strobe synchronous circuit 8 cannot output a strobe synchronizing signal even if the photography switch 6 is pushed. The second control circuit 22 receives the strobe synchronizing signal and outputs an observation to record changing signal for changing a displayed image from an observation image to a record image to the display selection circuit 2. At the same time, the second control circuit 22 outputs a strobe emission signal to the strobe 7.

The action of the second embodiment will now be described with reference to the flow chart shown in FIG. 3.

The electric power is first supplied to the fundus camera 101 (S. 1) and then is supplied to the still video recorder 4 (S. 2). After that, the photography switch 6 is pushed once (S. 3). Thereby, a selection signal is output. The first control circuit 21 receives this signal and then outputs a record-to-observation changing signal to the display selection circuit 2. If an observation image is displayed on the monitor 5, the observation image continues to be displayed without any change. If a record image is displayed thereon, the record image is changed to the observation image. When the second control circuit 22 receives a strobe synchronizing signal, the second control circuit 22 outputs an observation-to-record changing signal for changing from the observation image to the record image to the display selection circuit 2. However, if the still video recorder 4 is in an initial condition due to, for example, preheating, no strobe synchronizing signal is output even if signals generated by the operation of the photography switch 6 are input to the still video recorder 4 many times. The first control circuit 21 only outputs the record-to-observation changing signal to the display selection circuit 2 (S. 4). Consequently, the monitor 5 continues displaying the observation image. In order to give the operator warning, the monitor 5 may display the warning phrase "IN INITIAL CONDITION" at that time.

When several seconds elapse and the preheating is completed, the initial condition is removed. Thereby, the the still video recorder 4 is brought to the recordable condition (S. 5). When the photography switch 6 is again pushed under the recordable condition (S. 6), the first control circuit 21 outputs a record-to-observation changing signal to the display selection circuit 2 (S. 7). However, since the observation image is displayed on the monitor 5, the observation image continues to be displayed.

At the same time, the first control circuit 21 outputs a signal of the photography switch 6 to the still video recorder 4. According to the signal sent from the first control circuit 21, the operation changing means of the still video recorder 4 changes the condition of the still video recorder 4 from the recordable condition to the electronic image recording condition (S. 8). Thereby, the strobe synchronous circuit 8 outputs a strobe synchronizing signal to the second control circuit 22. According to the strobe synchronizing signal, the second control circuit 22 outputs a strobe emission signal to the strobe 7. Thereby, the strobe 7 emits a flash of light (S. 10). Simultaneously with the emission, an observation-to-record changing signal is input to the display selection circuit 2, and then the observation image displayed on the monitor 5 is changed to the record image (S. 9). When the photography switch 6 is again pushed, the record image displayed on the monitor 5 in changed to the observation image. A strobe synchronizing signal is not output at that time because the strobe synchronizing signal is output only under the recordable condition.

Consequently, when an alternate change is made between the observation image and the record image, the strobe 7 can always emit a flash of light at the most effective moment of time, and therefore photography is advantageously carried out.

FIG. 4 is a flow chart for explaining the action in a case in which a video printer is used for the electronic image recording portion of the fundus camera 101 of the second embodiment. Since the action is almost the same as in the case in which the still video recorder 4 is used for the electronic image recording portion, a detailed description of it is omitted.

In the second embodiment, a two-stroke switch as the photography switch 6 may be used. That is, when the two-stroke switch is pushed by a first stroke (half push), an image changing signal is output by the first control circuit 21, and a record-to-observation changing signal is output from the first control circuit 21 to the display selection circuit 2. On the other hand, when the two-stroke switch is pushed by a second stroke (full push), a signal for making an alternate change between the recordable condition and the image recording condition is output by the still video recorder 4 through the first control circuit 21.

In that case, if the monitor 5 displays the record image before photography, the two-stroke switch is pushed by the first stroke to turn on and, as a result, the record image displayed on the monitor 5 is changed to the observation image. When the two-stroke switch is further pushed by the second stroke, photography, recording, and strobe emission are synchronized with each other.

Third Embodiment

Figure 5:
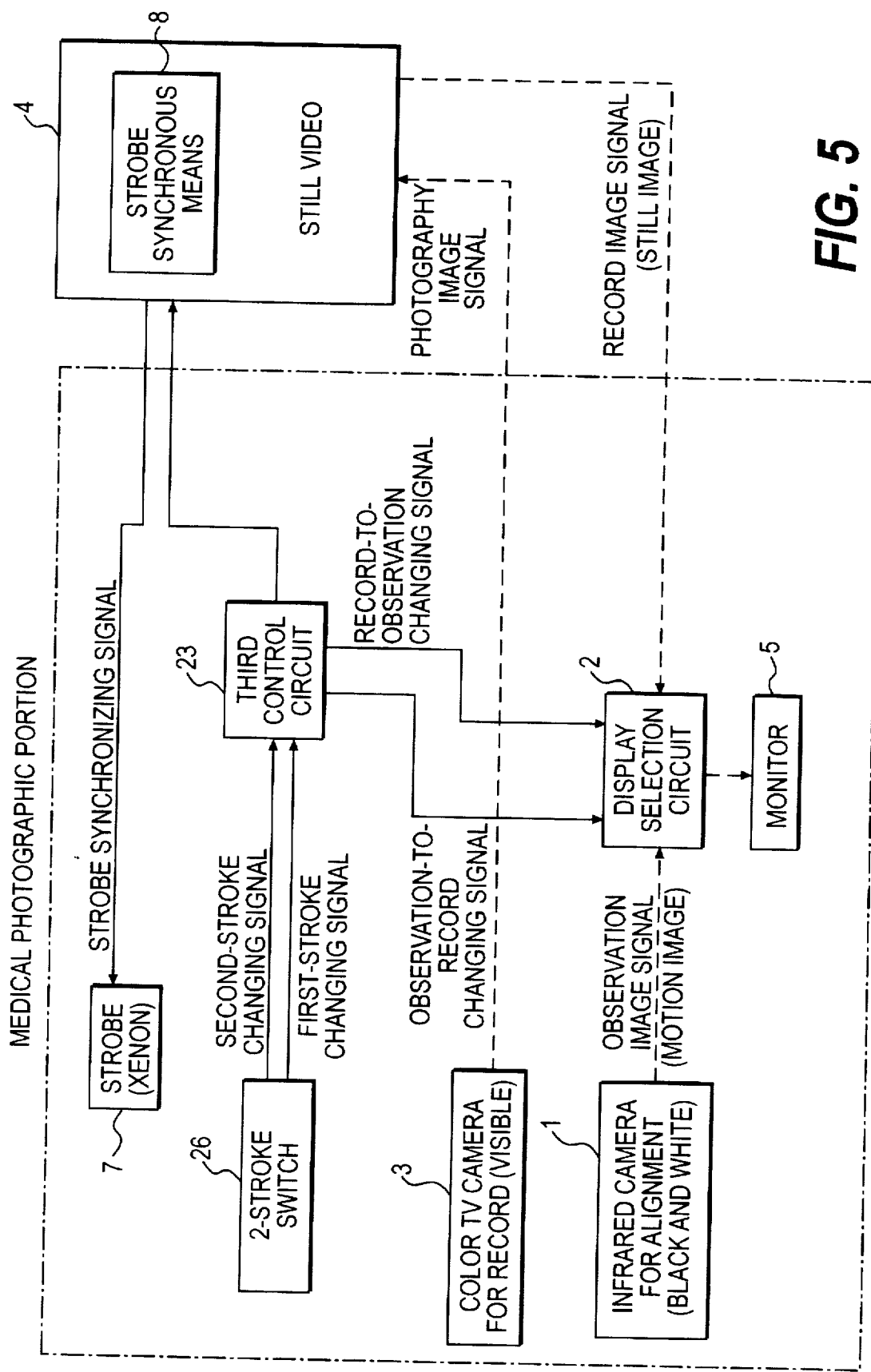
FIG. 5 is a block diagram schematically showing the construction of a medical photographic instrument according to a third embodiment of the present invention.

FIG. 5 shows a third embodiment of the present invention. In this embodiment, the aforementioned two-stroke switch is connected to a simple circuit.

An image changing signal generated when the two-stroke switch 26 is pushed by the first stroke (half push) is output to a third control circuit 23, and a record-to-observation changing signal is output from the third control circuit 23 to the display selection circuit 2. A second-stroke changing signal generated when the two-stroke switch 26 is pushed by the second stroke (full push) is used to make an alternate change between the recordable condition and the image recording condition. The third control circuit 23 outputs the second-stroke changing signal to the still video recorder 4. When receiving the second-stroke changing signal, the third control circuit 23 also outputs an observation to record changing signal to the display selection circuit 2.

For this reason, if the monitor 5 displays the record image before photography, the record image is changed to the observation image by the first stroke (half push) of the two-stroke switch 26. When the two-stroke switch 23 is further pushed by the second stroke (full push), the observation image is changed to a photography and record image and, at the same time, the strobe emits a flash of light synchronously. If the monitor 5 displays the observation image before photography, the first stroke of the two-stroke switch 26 does not bring about a change of the displayed image from the observation image to the record image because of the record-to-observation changing image output by the third control circuit 23.

Therefore, irrespective of the image displayed on the monitor 5, one stroke of the two-stroke switch 26 brings about the removal of the state in which a record image is displayed before photography, thereby leading to the display and photography of the observation image. Consequently, operational facility can be improved using the simple circuit.

In the first, second, and third embodiments, the strobe synchronous means 8 is constructed to, according to a display changing signal, output a strobe emission signal every other time in relation to the recording of a displayed image. Instead, the strobe synchronous means 8 may output a strobe synchronizing signal whenever the strobe synchronous means 8 receives a display changing signal. In that case, it is desirable that the second control circuit 22 is constructed to output a strobe synchronizing signal to the strobe 7 every other time and output an observation-to-record changing signal to the display selection circuit 2.

Fourth Embodiment

Figure 6:
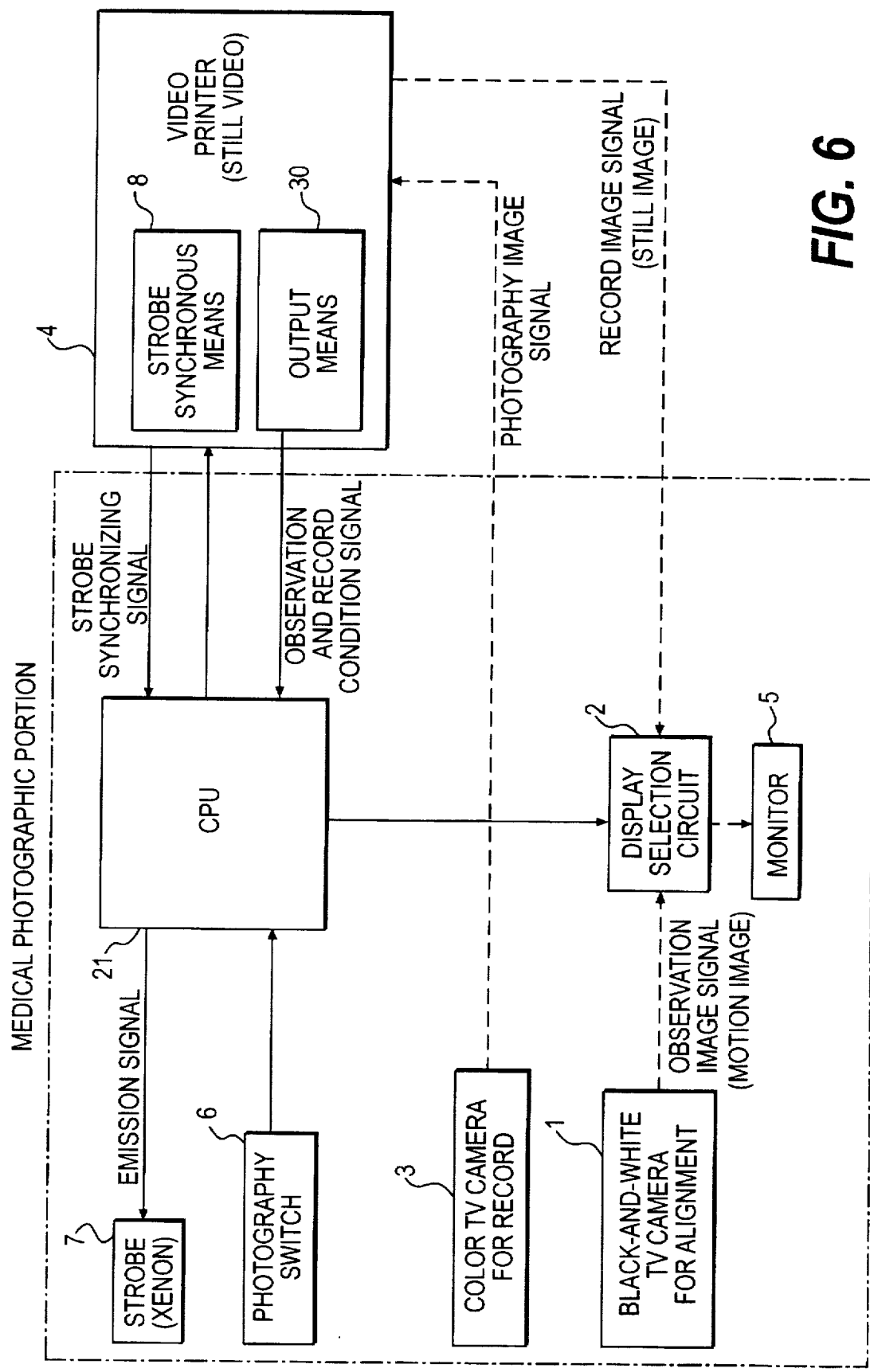
FIG. 6 is a block diagram schematically showing the construction of a medical photographic instrument according to a fourth embodiment of the present invention.
Figure 7:
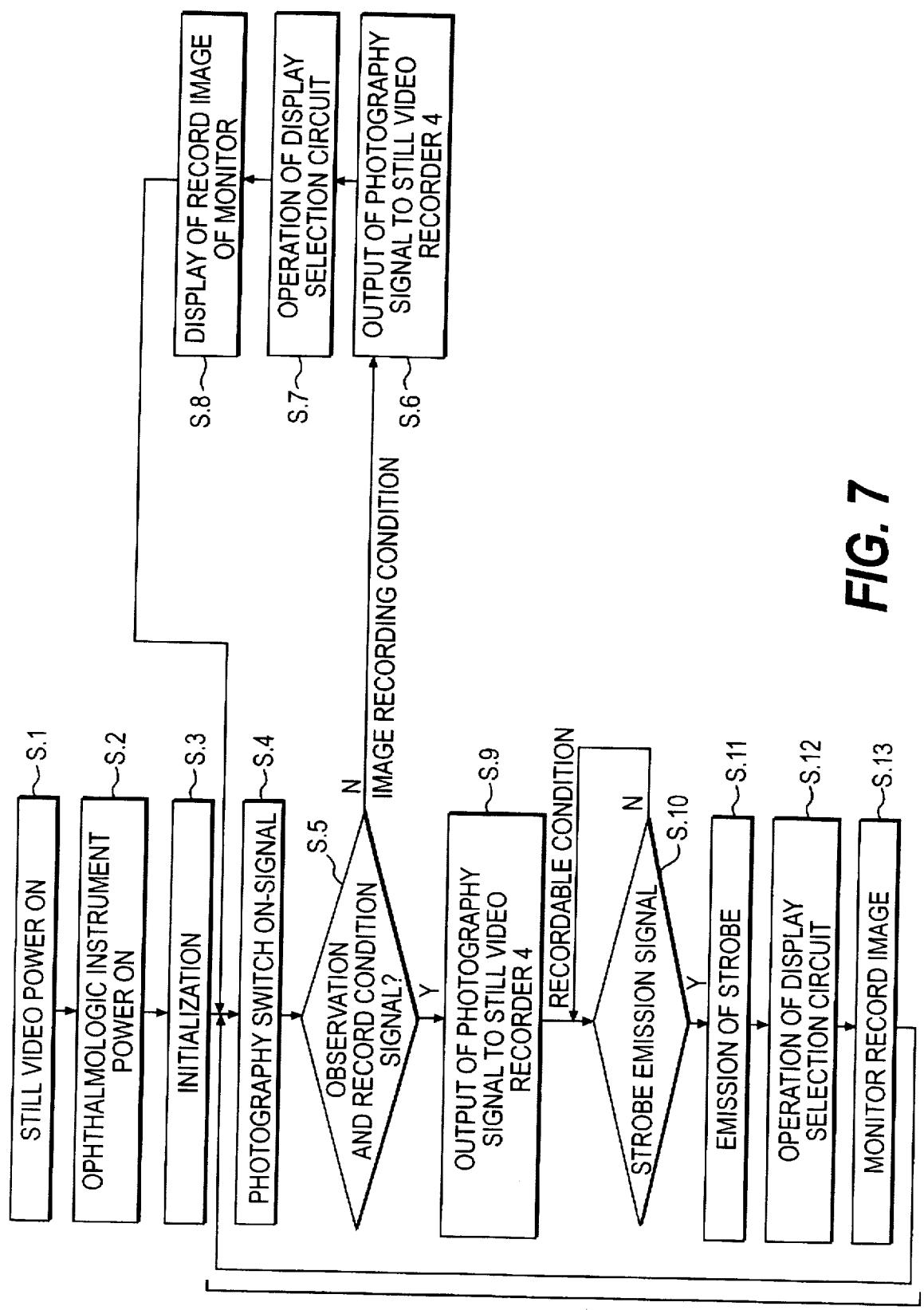
FIG. 7 is a flow chart of the action of the medical photographic instrument according to the fourth embodiment.

FIGS. 6 and 7 show a fundus camera according to a fourth embodiment of the present invention.

A detailed description of the same constituents as in the second embodiment is omitted. The difference between the second and fourth embodiments will be described.

The still video recorder 4 is connected to the photography switch 6 and the strobe 7 through a CPU 21. According to a signal from the photography switch 6 and an observation and record condition signal, the CPU 21 determines whether an observation image displaying state of the monitor 5 is changed to a record image displaying state thereof and vice versa. The CPU 21 outputs a record-to-observation changing signal to the display selection circuit 2. At the same time, according to the signal from the photography switch 6, the CPU 21 outputs a photography changing signal to the still video recorder 4.

The still video recorder 4 includes an operation changing means for making an alternate change between the recordable condition and the image recording condition according to the photography changing signal output by the the CPU 21 whenever the photography switch 6 is pushed. The observation and record condition signal is constantly output by an output means 30 when the still video recorder 4 is in the recordable condition and in the image recording condition. The observation and record condition signal is used to make a distinction between the image recording condition and the recordable condition.

When the still video recorder 4 receives the photography changing signal in the recordable condition, the strobe synchronous means 8 outputs strobe synchronizing signals to the CPU 21 for a given period of time.

The action of the fourth embodiment will now be described with reference to FIG. 7.

The still video recorder 4 is switched on (S. 1), and then the fundus camera is switched on (S. 2).

INITIALIZATION (S. 3)

The CPU 21 judges whether the observation and record condition signal is in the recordable condition or not. When the observation and record condition signal is in the image recording condition, the CPU 21 outputs a photography changing signal to the still video recorder 4. Thereby, the still video recorder 4 is brought to the recordable condition. Until completion of the initialization, the CPU 21 inhibits the output of an emission signal to the strobe 7. When the still video recorder 4 cannot output the observation and record condition signal because of its initial condition, the CPU 21 causes the monitor 5 to display the observation image until the output of the observation and record condition signal. However, the CPU 21 inhibits the reception of a signal from the photography switch 6. In order to give the operator warning, the monitor 5 may display a warning phrase as in the first embodiment. After the completion of initialization, the still video recorder 4 is brought to the recordable condition. In case the operator forgets to switch on the still video recorder 4, the same action is taken.

In this initialization, a given relationship is formed between the fundus camera 101 and the still video recorder 4.

PHOTOGRAPHIC ACTION

Whenever the photography switch 8 is pushed (S. 4), the CPU 21 detects a signal generated by the operation of the photography switch 6. When an observation and record condition signal is in the image recording condition, the CPU 21 output a signal to the display selection circuit 2 (S. 5). Thereby, an observation image is displayed on the monitor 5 and, at the same time, a photography changing signal is output to the still video recorder 4 (S. 6). Thereby, the still video recorder 4 is brought to the recordable condition (S. 7 and S. 8). When the observation and record condition signal is in the recordable condition, a photography changing signal is output to the still video recorder 4 (S. 9). The CPU 21 determines whether a strobe emission signal exists or not (S. 10), and thereby the strobe synchronous means 8 outputs a strobe synchronizing signal to the CPU 21. According to the strobe synchronizing signal, the CPU 21 outputs an emission signal to the strobe 7. Thereby, the strobe 7 emits a flash of light (S. 11). After the emission, the still video recorder 4 is brought to the image recording condition (S. 12). Next, the CPU 21 outputs a signal to the display selection circuit 2 so that the monitor 5 can display the record image (S. 13). This action is repeated every time the photography switch 6 is pushed.

In the fourth embodiment, information about the observation and record conditions is designed to be output from the still video recorder 4 to the CPU 21. Instead, another arrangement may be adopted in which a medical photographic portion detects the condition of the still video recorder 4 or, to the contrary, the still video recorder 4 detects the condition of the medical photographic portion.

As mentioned above, in the fourth embodiment, the invention is applied to the fundus camera 101. Instead, it can be applied to a slit lamp, a corneal endothelium photographing instrument, or an operation microscope.

Fifth Embodiment

There are some cases where the following disadvantage occurs to the medical photographic instrument of the first embodiment. For example, let it be supposed that when the medical photographic portion displays a record image, the monitor 5 is turned off by the performance of a power saving function in spite of an ON-state of a main power source of the medical photographic portion and therefore the operator turns off only the video printer 4 by operator's misunderstanding that the rain power source is in an OFF-state. If the power saving function is removed in that situation, the medical photographic portion is brought to a record image displaying condition. If the operator turns on the power source of the video printer 4 without awareness of it, the video printer 4 is brought to the recordable condition after the completion of the initial condition and therefore the relationship between the medical photographic portion and the electronic image recording portion is impaired.

In other words, although the electronic image recording portion is in the recordable condition, the monitor 5 is brought to the observation image displaying condition and therefore cannot display the record image. Further, when the photography switch 6 is pushed, a strobe synchronizing signal is output because of the recordable condition of the electronic image recording portion and, as a result, the strobe 7 emits a flash of light against operator's intention of no photography.

On the other hand, let it be supposed that the main power source of the medical photographic portion is turned off when the power source of the electronic image recording portion is in an ON-state. If the electronic image recording portion is in the image recording condition, the medical photographic portion is brought to the observation image displaying condition by turning on the main power source. However, a strobe synchronizing signal is not output by one push to the photography switch 6 because of the image recording condition of the electronic image recording portion.

Figure 8:
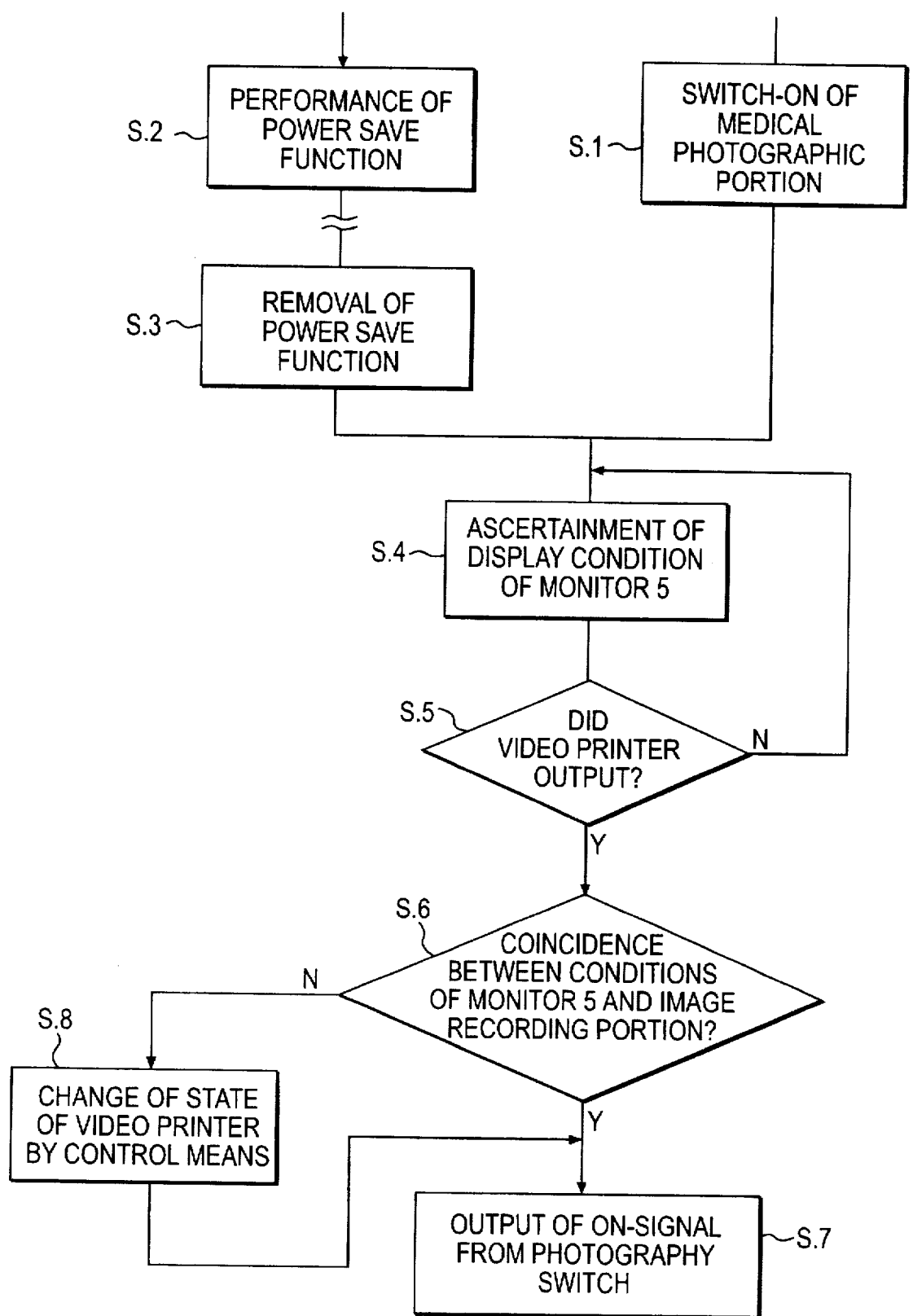
FIG. 8 is a flow chart of the action of a medical photographic instrument according to a fifth embodiment of the present invention.

One embodiment for resolving this kind of disadvantage will now be described with reference to a flow chart shown in FIG. 8. The action shown in FIG. 8 is accomplished by using the block circuit shown in FIG. 6.

In the fifth embodiment, the power source of the fundus camera of the medical photographic portion is turned on (S. 1). When a given period of time elapses, the power saving is performed (S. 2), and then the display of the monitor 5 fades out. A given period of time elapses in this state. The photography switch 6 is operated and then the base is moved. Thereby, the power saving is removed (S. 3). The control means (CPU 21) of the medical photographic portion determines whether the monitor 5 is in the observation image displaying condition or in the record image displaying condition (S. 4). Next, the control means (CPU 21) determines whether the video printer 4 has output a signal or not (S. 5). The output means of the video printer 4 outputs no signal during the initial condition of the video printer 4. The control means (CPU 21) determines whether the display state of the monitor 5 coincides with the state of the electronic image recording portion or not if the observation and record condition signal is input from the output means 30 of the video printer 4 (S. 6). When the monitor 5 is in the observation image displaying condition and the electronic image recording portion is in the image recording condition or when the monitor 5 is in the record image displaying condition and the electronic image recording portion is in the recordable condition, the control means judges that the display state of the monitor 5 differs from the state of the electronic image recording portion. The control means outputs a photography changing signal (photography switch turning-on signal) when the display state of the monitor 5 coincides with the state of the electronic image recording portion, namely, when the monitor 5 is in the observation image displaying condition and the electronic image recording portion is in the recordable condition or when the monitor 5 is in the record image displaying condition and the electronic image recording portion is in the image recording condition (S. 7). Further, the control means changes the state of the video printer 4 according to the photography changing signal when the display state of the monitor 6 differs from the state of the electronic image recording portion (S. 8). Thereby, the state of the electronic image recording portion is caused to coincide with the display state of the medical photographic portion. After that, the control means outputs the photography changing signal (photography switch turning on signal) (S. 7).

The display state of the medical photographic portion can be controlled to coincide with the state of the electronic image recording portion according to the observation and record condition signal output by the output means 30.

What is claimed is:

1. A medical photographic instrument comprising:

a medical photographic portion; and an electronic image recording portion;

said medical photographic portion comprising:
  display means for displaying an observation image for alignment and a record image recorded in said electronic image recording portion; and display selecting means for causing said display means to display said observation image and said record image alternately;

said electronic image recording portion comprising:
  operation changing means for making an alternate change between a recordable state of said electronic image recording portion and an image recording state of said electronic image recording portion according to a selection signal output by said medical photographic portion; and strobe synchronous means for outputting a strobe synchronizing signal according to which a strobe emits a flash of light when said recordable state is changed to said image recording state;

said display selecting means receiving:
  a record-to-observation changing signal according to said selection signal output by said medical photographic portion; and an observation-to-record changing signal according to said strobe synchronizing signal;

said display means being brought to an observation image displaying state when said display selecting means receives said record-to-observation changing signal only, and said display means being brought to a record image displaying state when said display selecting means receives both of said record-to-observation changing signal and said observation-to-record changing signal.

* * * * *

UNITED STATES PATENT AND TRADEMARK OFFICE
CERTIFICATE OF CORRECTION

PATENT NO. : 5,768,465
DATED : June 16, 1998
INVENTOR(S) : Sugawara et al.

It is certified that error appears in the above-identified patent and that said Letters Patent is hereby corrected as shown below:

In Claim 1, col. 11, line 27, after "photographic portion", insert --including display means for displaying an observation image for alignment and a record image recorded as an electronic image, display selecting means for causing said display means to display said observation image and said record image alternately, and a photography switch--; and delete "and".

In Claim 1, col. 11, line 28, after "recording portion", insert --including operation changing means for making an alternate change between a recordable state and an image recording state and a strobe synchronous circuit for outputting a strobe synchronizing signal for causing a strobe to emit a flash of light only when said recordable state is changed to said image recording state; a first control circuit operated by said photography switch for outputting to said electronic image recording portion, an operation changing signal for actuating said operation changing means, and for outputting to said display selecting means, a record-to-observation changing signal for changing an image displayed on said display means from said record image to said observation image; and a second control circuit for outputting to said display selecting means in accordance with generation of said strobe synchronizing signal, an observation-to-record signal for changing an image displayed on said display means from said observation image to said record image.--; and delete ";".

UNITED STATES PATENT AND TRADEMARK OFFICE
CERTIFICATE OF CORRECTION

PATENT NO. : 5,768,465
DATED : June 16, 1998
INVENTOR(S) : Sugawara et al

It is certified that error appears in the above-identified patent and that said Letters Patent is hereby corrected as shown below:

In Claim 1, col. 11, delete lines 29-32 in their entirety; and

In Claim 1, col. 12, delete lines 1-30 in their entirety.

Signed and Sealed this

Seventh Day of December, 1999

*Attest:*

Q. TODD DICKINSON

*Attesting Officer*        *Acting Commissioner of Patents and Trademarks*